United States Patent
Voegele et al.

(10) Patent No.: US 6,220,248 B1
(45) Date of Patent: Apr. 24, 2001

(54) METHOD FOR IMPLANTING A BIOPSY MARKER

(75) Inventors: James W. Voegele; Michael Dolgin, both of Cincinnati; Kenneth S. Wales, Mason, all of OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 09/176,557

(22) Filed: Oct. 21, 1998

(51) Int. Cl.[7] .................................................. A61B 19/00
(52) U.S. Cl. .......................... 128/898; 604/116; 600/567
(58) Field of Search ...................... 604/115, 116, 604/117, 164.01, 164.02; 600/567; 128/898

(56) References Cited

U.S. PATENT DOCUMENTS

| | | | |
|---|---|---|---|
| 4,080,959 | 3/1978 | Leveen | 128/2 H |
| 4,649,151 | 3/1987 | Dougherty et al. | 514/410 |
| 4,733,664 | 3/1988 | Kirsch et al. | 128/334 |
| 5,147,307 | 9/1992 | Gluck | 604/116 |
| 5,192,270 | 3/1993 | Carswell, Jr. | 604/116 |
| 5,221,269 | 6/1993 | Miller et al. | 604/281 |
| 5,240,011 | 8/1993 | Assa | 128/751 |
| 5,902,310 | * 5/1999 | Foerster et al. | 606/142 |

FOREIGN PATENT DOCUMENTS

| | | |
|---|---|---|
| 1641297 | * 4/1991 | (SU) . |
| WO 9608208A1 | 3/1996 | (WO) . |

OTHER PUBLICATIONS

The Geographic Cluster of Microcalcifications of the Breast, Marc J. Homer, M.D., Douglas J. Marchant, M.D., F.A.C.S., and Thomas J. Smith, M.D., Boston, Massachusetts, pp. 532–534 From the Department of Radiology, The Department of Obstetrics and Gynecology and Surgery, and the Division of Surgical Oncology, New England Medical Center and the Tufts University School Of medicine, Boston.

A Permanent Radiopaque Marker Technique for the Study of Pharyngeal Swallowing in Dogs, Sandra S. Kramer, M.D., James H. Anderson, Ph.D., John D. Strandgerg, D.V.M., and Martin W. Donner, M.D. Russell H. Morgan Department of Radiology and Radiological Science and Division of Comparative Medicine, The Johns Hopkins Medical Institutions, Baltimore, Maryland, USA.

* cited by examiner

Primary Examiner—Dinh X. Nguyen

(57) ABSTRACT

A method for implanting a biopsy marker at a biopsy site within bodily tissue is disclosed. A marker applier is provided which has a marker cannula for receiving the biopsy marker. The marker cannula has a lateral marker window, and the marker is positioned at the window for ejection therefrom. The marker applier also has an ejector rod moveable longitudinally in the marker cannula which, when actuated, forces the ejection of the biopsy marker from the marker cannula through the window and into the tissue. The marker applier is inserted into a biopsy cannula positioned at the biopsy site. The biopsy cannula also has a lateral window, and it is necessary to orient the lateral marker window into alignment with the lateral biopsy window. Upon proper orientation, the ejector rod is actuated, and the biopsy marker is ejected from the marker cannula for implantation in the tissue in a direction substantially perpendicularly to the longitudinal movement of the ejector rod. This method is particularly useful for implantation of a marker at a breast biopsy site to mark the location of the breast biopsy during and after the biopsy procedure.

6 Claims, 18 Drawing Sheets

METHOD FOR IMPLANTING A BIOPSY MARKER

BACKGROUND OF THE INVENTION

This invention relates to a method for implanting a marker in tissue of a surgical patent at a biopsy site. More specifically, it relates to such a method to implant a marker for the purpose of defining particular locations in human tissue during and after a biopsy procedure, particularly in a human breast.

One in nine American women will develop breast cancer in their lifetime. It is the leading cause of cancer deaths in women 40–55 years of age and the second leading cause of cancer deaths in women overall. Breast cancer will be diagnosed in approximately one in eight women in their lifetime, and one in 30 will die of this disease. Breast cancer does occur in males but is much less common. Biopsy requests stem from a screening process generally performed via a physical examination (palpable) and/or mammogram (non-palpable). A biopsy is indicated if suspicious tissue is detected. Five out of six biopsies performed return benign indications.

It is desirable and often necessary to perform procedures for detecting, sampling, and testing lesions and other abnormalities in the tissue of humans and other animals, particularly in the diagnosis and treatment of patients with cancerous tumors, pre-malignant condition and other diseases or disorders. Typically, in the case of cancer, when a physician establish by means of known procedures (i.e. palpation, x-ray, MRI, or ultrasound imaging) that suspicious circumstances exist, a biopsy is performed to determine whether the cells are cancerous. Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination, which may be done via a frozen section or paraffin section. The chief difference between FNA and core biopsy is the size of the tissue sample taken. An imaging system having spectroscopic capabilities, such as the stereotactic guidance system described in U.S. Pat. No. 5,240,011 is employed to guide the extraction instrument to the lesion.

Depending on the procedure being performed, the sample may result in the suspicious lesion being partially or completely removed. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from dead abnormal tissue, which may be cancerous or precancerous, and it is desirable to remove only a sample of the lesion, rather than the entire lesion, to evaluate it. This is because such a lesion actually serves to mark or define the location of adjacent abnormal tissue, so the physician does not wish to remove the entire lesion and thereby lose a critical means for later relocating the affected tissue. One of the benefits to the patient from core biopsy is that the mass of the tissue taken is small. However, oftentimes, either inadvertently or because the lesion is too small, the entire lesion is removed for evaluation, even though it is desirable to remove only a portion. Then, if subsequent analysis indicates the tissue to be malignant (malignant tissue requires removal, days or weeks later, of tissue around the immediate site of the original biopsy), it is difficult for the physician to determine the precise location of the lesion, in order to perform necessary additional procedures on adjacent potentially cancerous tissue. Additionally, even if the lesion is found to be benign, there will be no evidence of its location during future examinations, to mark the location of the previously removed calcification so that the affected tissue may be carefully monitored for future reoccurrence.

Thus, it would be of considerable benefit to be able to permanently mark the location or margins of such a lesion prior to or immediately after removing the sample. Marking prior to removal would help to ensure that the entire lesion is excised, if desired. Alternatively, if the lesion were inadvertently removed in its entirety, marking the biopsy site immediately after the procedure would enable re-establishment of its location for future identification.

A number of procedures and devices for marking and locating particular tissue locations are known in the prior art. For example, location wire guides, such as that described in U.S. Pat. No. 5,221,269 to Miller et al, are well known for locating lesions, particularly in the breast. The device described by Miller comprises a tubular introducer needle and an attached wire guide, which has at its distal end a helical coil configuration for locking into position about the targeted lesion. The needle is introduced onto the breast and guided to the lesion site using an imaging system of a known type, for example, x-ray, ultrasound or magnetic resonance imaging (MRI), at which time the helical coil at the distal end is deployed about the lesion. Then, the needle may be removed from the wire guide, which remains in a locked position distally about the lesion for guiding a surgeon down the wire to the lesion site during subsequent surgery. While such a location system is effective, it is obviously intended and designed to be only temporary, and is removed once the surgery or other procedure has been completed.

Other devices are known for marking external regions of a patient's skin. For example, U.S. Pat. No. 5,192,270 to Carswell, Jr. discloses a syringe which dispenses a colorant to give a visual indication on the surface of the point at which an injection has or will be given. Similarly, U.S. Pat. No. 5,147,307 to Gluck discloses a device which has patterning elements for impressing a temporary mark in a patients skin, for guiding the location of an injection or the like. It is also known to tape or otherwise adhere a small metallic marker, e.g. a 3 millimeter diameter lead sphere, on the skin of a human breast in order to delineate the location of skin calcifications (see Homer et al, The Geographic Cluster of Microcalcifications of the Breast, Surgery, Gynecology, & Obstetrics, December 1985). Obviously, however, none of these approaches are useful for marking and delineating internal tissue abnormalities, such as lesions or tumors.

Still another approach for marking potential lesions and tumors of the breast is described in U.S. Pat. No. 4,080,959. In the described procedure, the skin of the portion of the body to be evaluated, such as the breasts, is coated with a heat sensitive color-responsive chemical, after which that portion of the body is heated with penetrating radiation such as diatherny. Then, the coated body portion is scanned for color changes which would indicate hot spots beneath the skin surface. These so-called hot spots may represent a tumor or lesion, which does not dissipate heat as rapidly because of its relatively poor blood circulation (about ½₀ of the blood flow through normal body tissue). This method, of course, functions as a temporary diagnostic tool, rather than in a permanent means for delineating the location of a tumor or lesion.

A method of identifying and treating abnormal neoplastic tissue or pathogens within the body is described in U.S. Pat. No. 4,649,151 to Doughety et al. In this method, a tumor-selective photosensitizing drug is introduced into a patient's body, where it is cleared from normal tissue faster than it is cleared from abnormal tissue. After the drug clears normal tissue but before it has cleared abnormal neoplastic tissue, the abnormal neoplastic tissue may be located by the luminescence of the drug within the abnormal tissue. The fluorescence may be observed with low intensity light, some of which is within the drug's absorbency spectrum. Once detected, the tissue may be destroyed by further application of higher intensity light having a frequency within the absorbency spectrum of the drug. Of course, this method also is only a temporary means for marking the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion, using an imaging system. Later, during the extraction procedure, the surgeon harvests a tissue sample from the stained tissue. However, while such staining techniques can be effective, it is difficult to precisely localize the stain. Also, the stains are difficult to detect flouoroscopically and may not always be permanent.

Additionally, it is known to implant markers directly into a patient's body using invasive surgical techniques. For example, during a coronary artery bypass graft (CABG), which of course constitutes open-heart surgery, it is common practice to surgically apply one or more metallic rings to the aorta at the site of the graft. This enables a practitioner to later return to the site of the graft by identifying the rings, for evaluative purposes. It is also common practice to mark a surgical site with staples, vascular clips, and the like, for the purpose of future evaluation of the site.

A technique has been described for the study of pharyngeal swallowing in dogs, which involves permanently implanting steel marker beads in the submucosa of the pharynx (S. S. Kramer et al, A Permanent Radiopaque Marker Technique for the Study of Pharyngeal Swallowing of Dogs, Dysphagia, Vol. 1, pp.163–167, 1987). The article posits that the radiographic study of these marker beads during swallowing on many occasions over a substantial period of time provides a better understanding of the pharyngeal phase of deglutition on humans. In the described technique, the beads were deposited using a metallic needle cannula having an internal diameter slightly smaller than the beads to be implanted. When suction was applied to the cannula, the bead sat firmly on the tip. Once the ball-tipped cannula was inserted through tissue, the suction was broken, thereby releasing the bead, and the cannula is withdrawn.

Of course, this technique was not adapted or intended to mark specific tissue sites, but rather to mark an entire region or structure of the body in order to evaluate anatomical movements (i.e. swallowing motions). It also was not intended for use in humans.

Accordingly, what is needed is a method and device for non-surgically implanting potentially permanent markers at the site of a lesion or other abnormal tissue, for the purpose of defining the margins of a lesion before it is removed and/or to establish its location after it has been removed. The markers should be easy to deploy and easily detected using state of the art imaging techniques.

A method of implanting markers directly into a patient's body using minimally invasive surgical techniques is described in International Patent No. WO 9608208A1 to Foerster et al. In this method, a clipping device is introduced to the lesion site by a tubular cannula. Once the clip is at the lesion site, an actuating means at the proximal end outside the patient deploys the clip into the tissue. This marking means can be used long term and can be imaged by most imaging techniques. However, because of it's small size, current ultrasound imaging systems are unable to detect is within the tissue.

Another method of implanting a marker is described in copending, commonly assigned application Ser. No. 08/802, 958, filed Feb. 21, 1997, and entitled "Apparatus and Method for Marking Tissue". The marker described in this method utilizes a central tang that is tensily loaded to cause a squarely supported, end contact bridge on the marker to bend resulting in the goal post arms to swing inward in an arcuate fashion to pinch tissue. The tensile load on the tang is increased until it breaks at a predetermined location leaving the marker attached to the tissue site. Unfortunately, this method requires the marker to be pulled away from tissue when the marker is formed, consequently, limiting marker penetration and the amount of tissue grasped. Additionally, the marker is delivered to the biopsy site when the marker applier is correspondingly delivered through the biopsy cannula which is used for taking the biopsy sample. It is necessary to properly orient the opening on the applier with the biopsy port on the biopsy cannula in order to properly deploy the marker at the biopsy site. Unfortunately, the method described in this pending application does not describe a technique for readily accomplishing the proper orientational alignment between the applier opening and the biopsy port.

A surgical clip for permanently joining opposed tissue for an anastomosis procedure is described in U.S. Pat. No. 4,733,664 to Kirsh et al. This is accomplished using an applier, also disclosed, to pull on a frangible central tang to close a pair of spaced arcuate arms extending generally parallel in one direction from opposite ends of the plastically deformable bridge. The arms are brought around opposed tissue. A predetermined force is applied to create a tensile break of the neck in the tang. Specific angles of clip shoulder and applier are given. The applier jaw faces are in the range of 120° to 180° with respect to one another, specifically 150° Unfortunately, the method of forming this clip suffers a fate similar to the method described in the preceding paragraph.

More recently, an applier for implanting a biopsy marker into tissue has been described in commonly assigned, copending application Ser. No. 09/105,570, filed Jun. 26, 1998, and entitled "Applier for Implantable Surgical Marker." Advantageously, the opening at the distal end of the applier described in this application can be properly oriented into alignment with the biopsy port on the biopsy cannula in a simple and effective way, eliminating timely trial and error. However, a drawback of the applier specifically illustrated and others described in the art is that since the marker is ejected in a direction parallel to the longitudinal axis of the applier, it is necessary to initially push the applier distally so that its distal end protrudes from the biopsy port prior to implanting the marker in the tissue. This added step is inconvenient.

Accordingly, what is needed is a method for delivering a biopsy marker to a site of a surgical biopsy, and implanting the marker at the site. Ideally, the method would eliminate the need to push the distal end of the applier out of the biopsy port before the marker is properly positioned for tissue implantation, consequently eliminating a step and saving time.

SUMMARY OF INVENTION

The invention is a method for implanting a biopsy marker at a biopsy site within bodily tissue. This method comprises four steps.

A marker applier having certain features is provided. The marker applier has a marker cannula for receiving the biopsy marker in the marker cannula. The marker cannula has a lateral marker window at a distal end of the marker cannula. The biopsy marker is positioned at the lateral marker window for ejection out of the lateral marker window.

The marker applier also has an elongated ejector rod movable longitudinally in the marker cannula. The ejector rod is cooperable with the biopsy marker for ejecting the biopsy marker out of the lateral marker window in a direction substantially perpendicularly to the elongated ejector rod upon longitudinal movement of the ejector rod.

The marker applier is inserted into a biopsy cannula positioned at the biopsy site. The biopsy cannula has a lateral biopsy window at a distal end of the biopsy cannula.

Once the marker applier is inserted into the biopsy cannula, the lateral marker window of the marker cannula of the marker applier is oriented into alignment with the lateral biopsy window of the biopsy cannula. The elongated ejector rod of the marker applier is then actuated for longitudinal movement of the ejector rod in the marker cannula. Upon actuation, the biopsy marker is ejected in a direction substantially perpendicularly relative to the elongated ejector rod. The biopsy marker is ejected from the marker cannula, through the lateral marker window and the lateral biopsy window, and into the bodily tissue at the biopsy site. In so doing, the marker is properly implanted at the biopsy site.

Significantly, the method for implanting the biopsy marker of this invention involves ejecting the marker in a direction substantially perpendicularly to the ejector rod of the marker applier. This manner of ejection of the biopsy marker enables ejection of the marker from the marker cannula and through the lateral marker window into the desired tissue without the need to push the distal end of the marker cannula of the applier out of the lateral biopsy window. Since it is unnecessary to position the distal end of the marker cannula so that it protrudes from the lateral biopsy window prior to ejection of the marker for implantation into tissue, a procedural step can be eliminated, consequently saving time and frustration.

The method of this invention can be used for delivering a biopsy marker to a site of a surgical biopsy, and subsequently implanting the marker at the site. In a particularly preferred embodiment of this invention, the method is used for implanting a biopsy marker at a site of a breast biopsy.

DETAILED DESCRIPTION OF THE PREFERRED EMBODIMENTS

Figure 1:
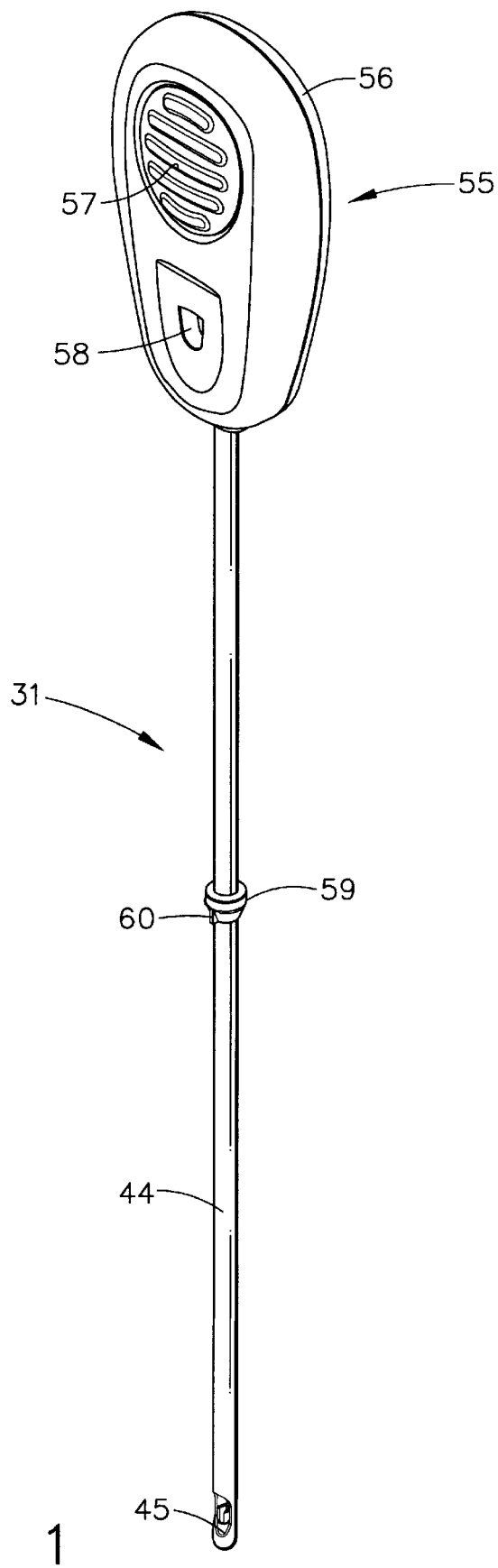
FIG. 1 is an isometric view of a preferred marker applier for use in accordance with a preferred method of this invention.
Figure 2:
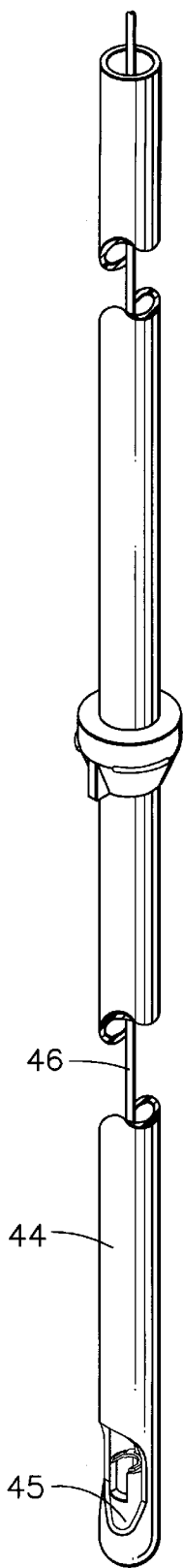
FIG. 2 is an enlarged and foreshortened isometric view of the distal end of the applier of FIG. 1.

Referring initially to FIGS. 2–6, there is illustrated a biopsy marker 30 in combination with a marker applier 31 for use in a first embodiment of the method of this invention. Focusing first on FIGS. 4 and 5, the biopsy marker is a marker which is symmetrical about its centerline axis. The marker has a pair of penetration tines 32 for facilitating the implantation of the marker into soft tissue. At the proximal end of the penetration tines are a pair of reverse migration cleats 33 for resisting unwanted migration of the implanted marker. The marker has a deformable link coupling the pair of penetration tines. The deformable link 34 is bounded on one side with a froward migration surface 35 and on its opposite side with a tapered surface 36. A pair of proximal surfaces 37 transition the deformable link from each of the penetration tines. Each of the proximal surfaces has a spreader tine 38.

Figure 3:
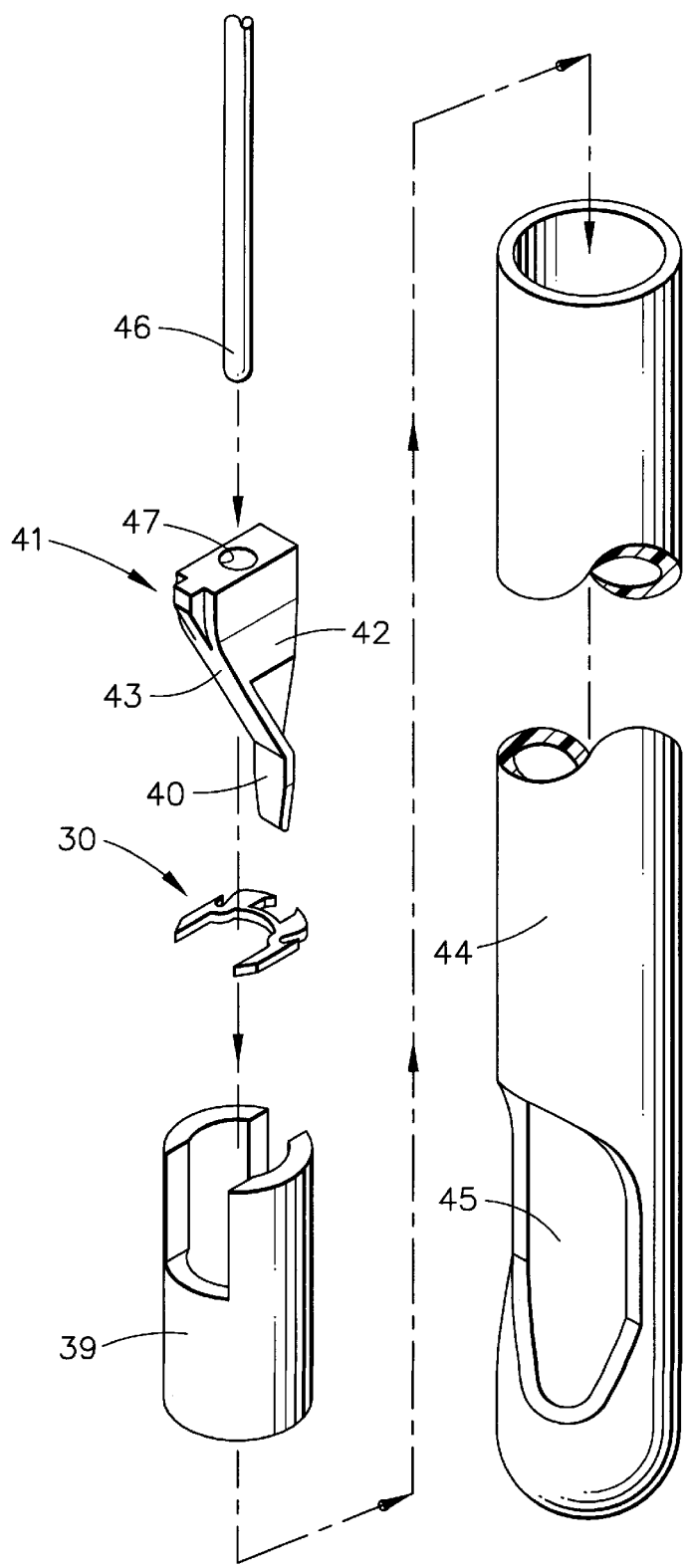
FIG. 3 is a further enlarged and exploded isometric view of the distal end of the marker applier of FIG. 1, including a preferred embodiment of a biopsy marker for use with the applier.
Figure 4:
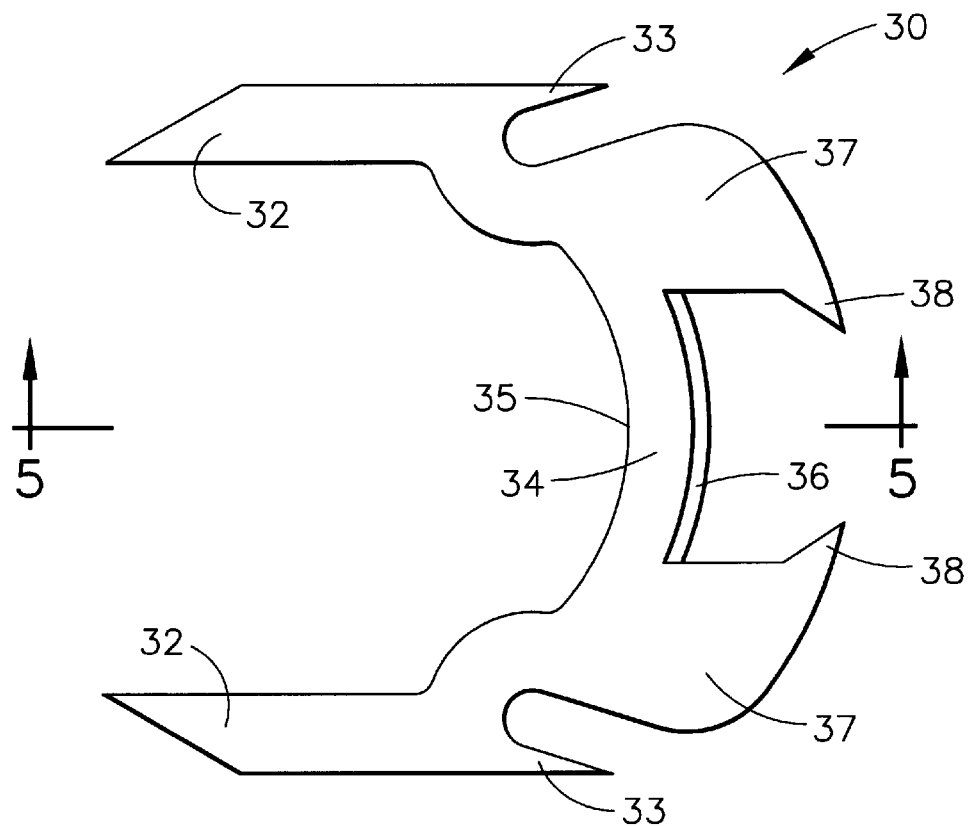
FIG. 4 is a plan view of the marker depicted in FIG. 3.
Figure 5:
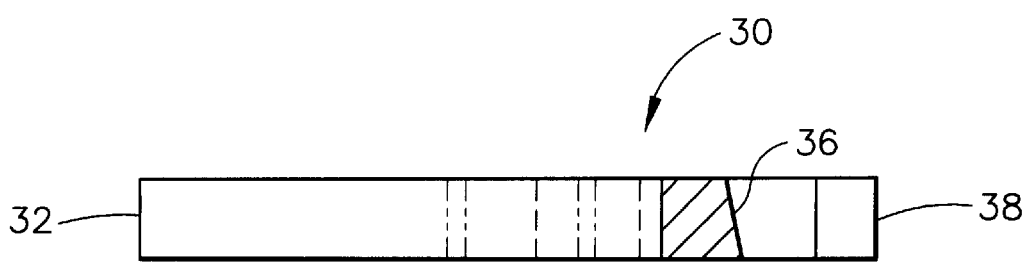
FIG. 5 is a section view taken along line 5—5 of FIG. 4.
Figure 6:
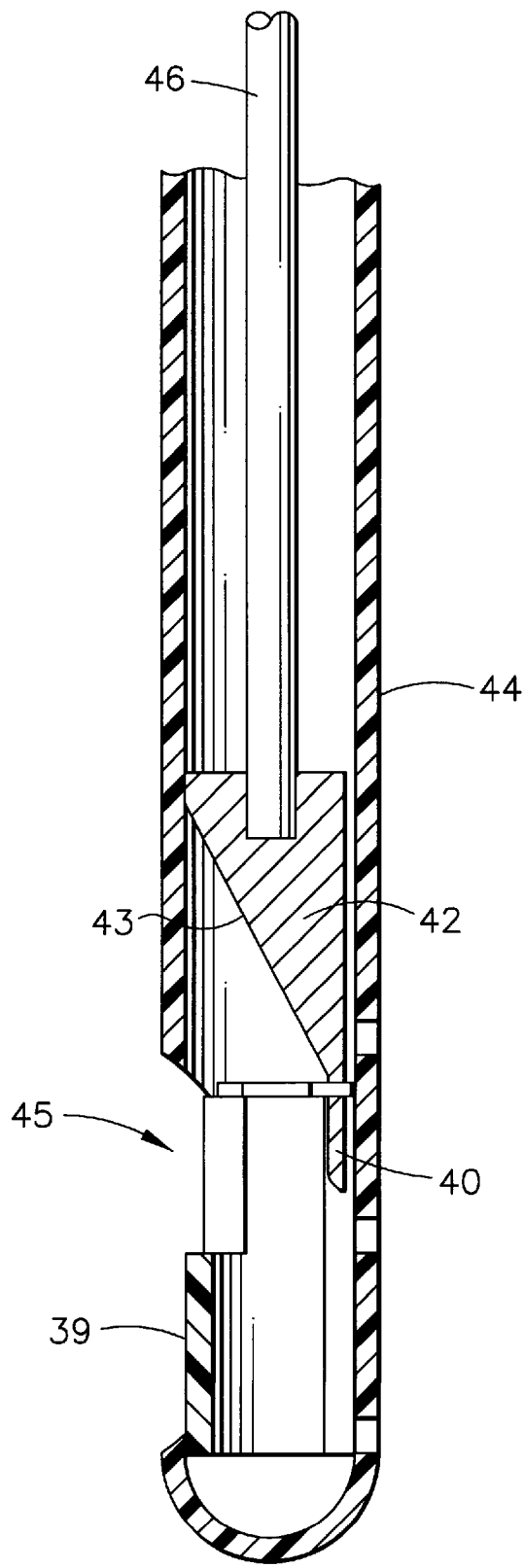
FIG. 6 is a side elevation view in section of the distal end of the applier shown in FIG. 2.
Figure 7:
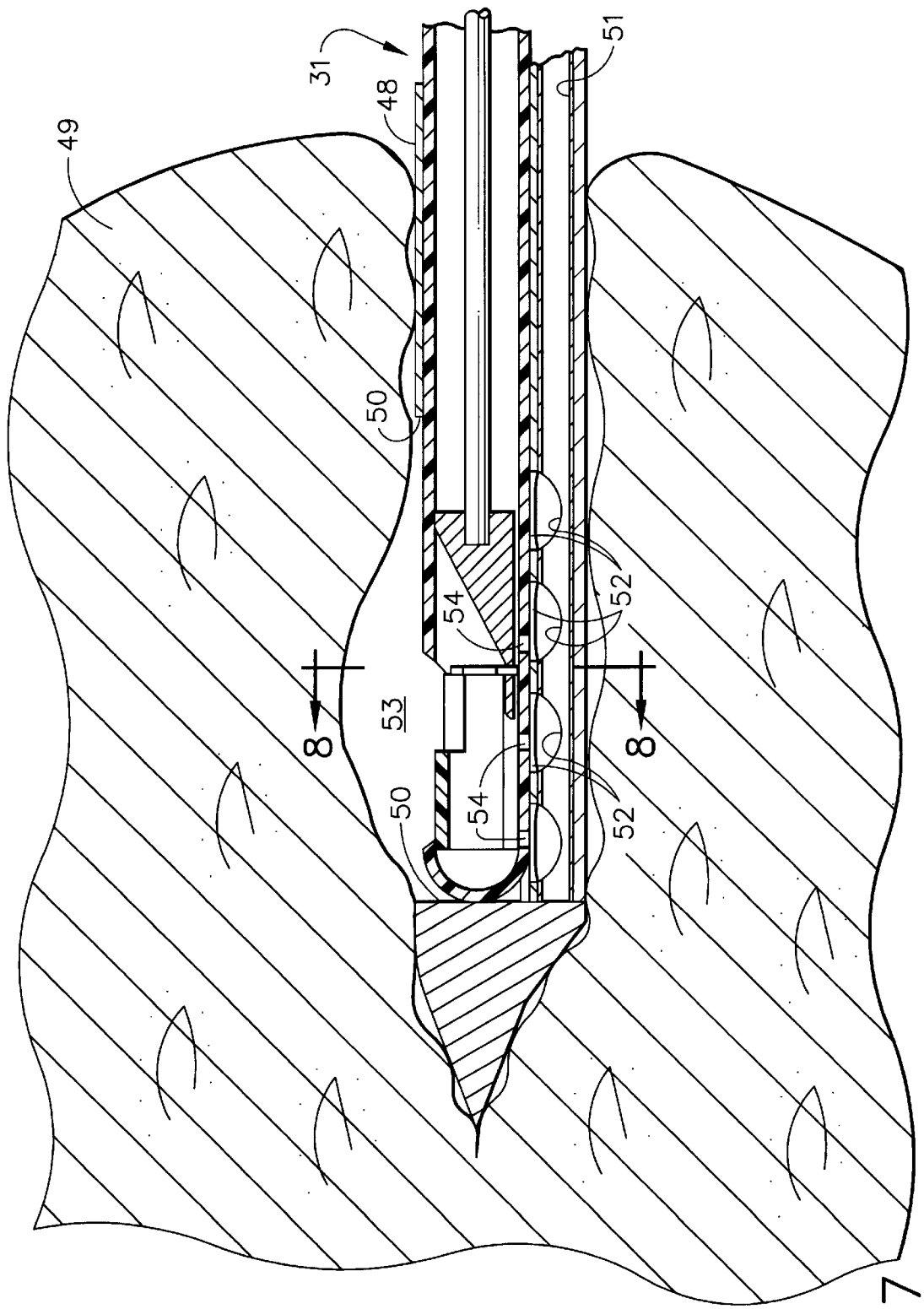
FIG. 7 is a side elevation view in section of the preferred marker applier of FIG. 1 inserted into a biopsy cannula positioned at a breast biopsy site.

Focusing now on FIG. 3, the marker applier has a marker backstop 39 for support of the marker while the marker is formed from its original open position to a closed position where the penetration tines of the biopsy marker are adjacent to each other upon implantation into tissue. The marker sits against the proximal surface of the marker backstop on a loading tongue 40 of an ejector shoe 41. The ejector shoe has a wedge surface 42 and a downwardly sloped ramp 43 transitioning to the loading tongue.

The biopsy marker, ejector shoe and marker backstop are positioned in an elongated, flexible marker cannula 44. The marker cannula has a lateral marker window 45 at its distal end. An elongated ejector push rod 46 is positioned for longitudinal movement within the marker cannula. The distal end of the push rod is fixed within an aperture 47 on the ejector shoe 41. Longitudinal movement of the push rod causes a corresponding longitudinal movement of the ejector shoe.

Referring now to FIGS. 7–13, there is illustrated the sequence of steps for using the marker in combination with the marker applier for use in the practice of the method of the first preferred embodiment of this invention. Focusing initially on FIG. 7, the marker applier 31 is initially inserted into a biopsy cannula 48 which is positioned at the biopsy site. In this particular illustration, the biopsy cannula has been inserted into breast tissue 49 for the removal of a breast biopsy. The biopsy cannula has a lateral biopsy window 50 at its distal end (see also FIG. 8). The biopsy cannula also includes a vacuum tube 51 having a plurality of vacuum tube ports 52 for drawing a vacuum through the lateral biopsy window to consequently draw tissue toward the window. The marker applier correspondingly has a plurality of cannula ports 54 in communication with the vacuum tube ports of the biopsy cannula.

Figure 8:
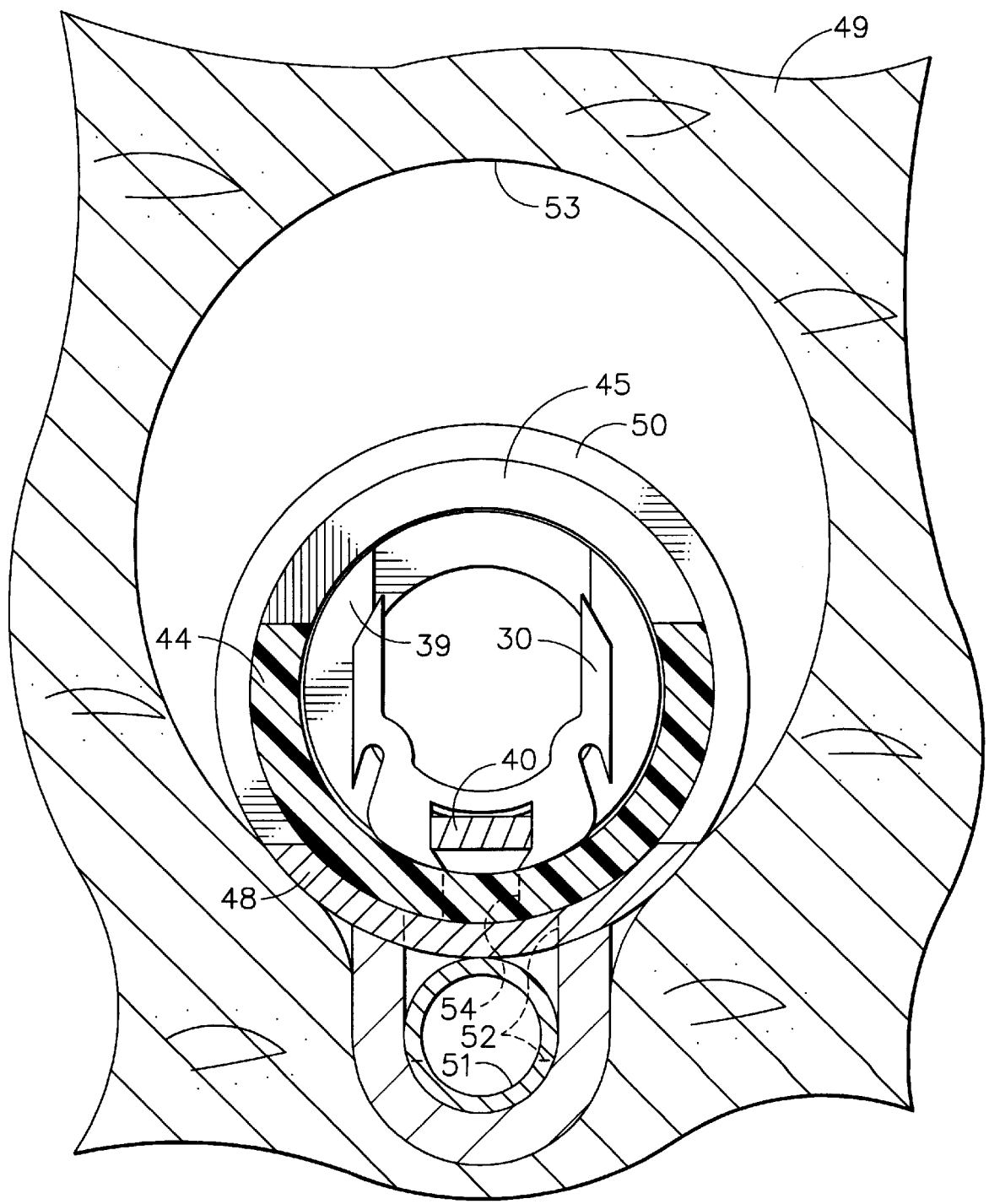
FIG. 8 is a view taken along line 8—8 of FIG. 7 illustrating the marker prior to ejection.

Looking at FIG. 8, the reader will observe that the lateral marker window of the marker cannula of the marker applier is oriented into alignment with the lateral biopsy window of the biopsy cannula. In this manner, there is a direct opening from the lateral marker window to the surgical site, thus exposing the biopsy marker from within the lateral marker window to the surgical site. The reader will also note that because a biopsy sample has already been taken from the surgical site, there is a sample cavity 53 separating the lateral biopsy window form the breast tissue.

Figure 9:
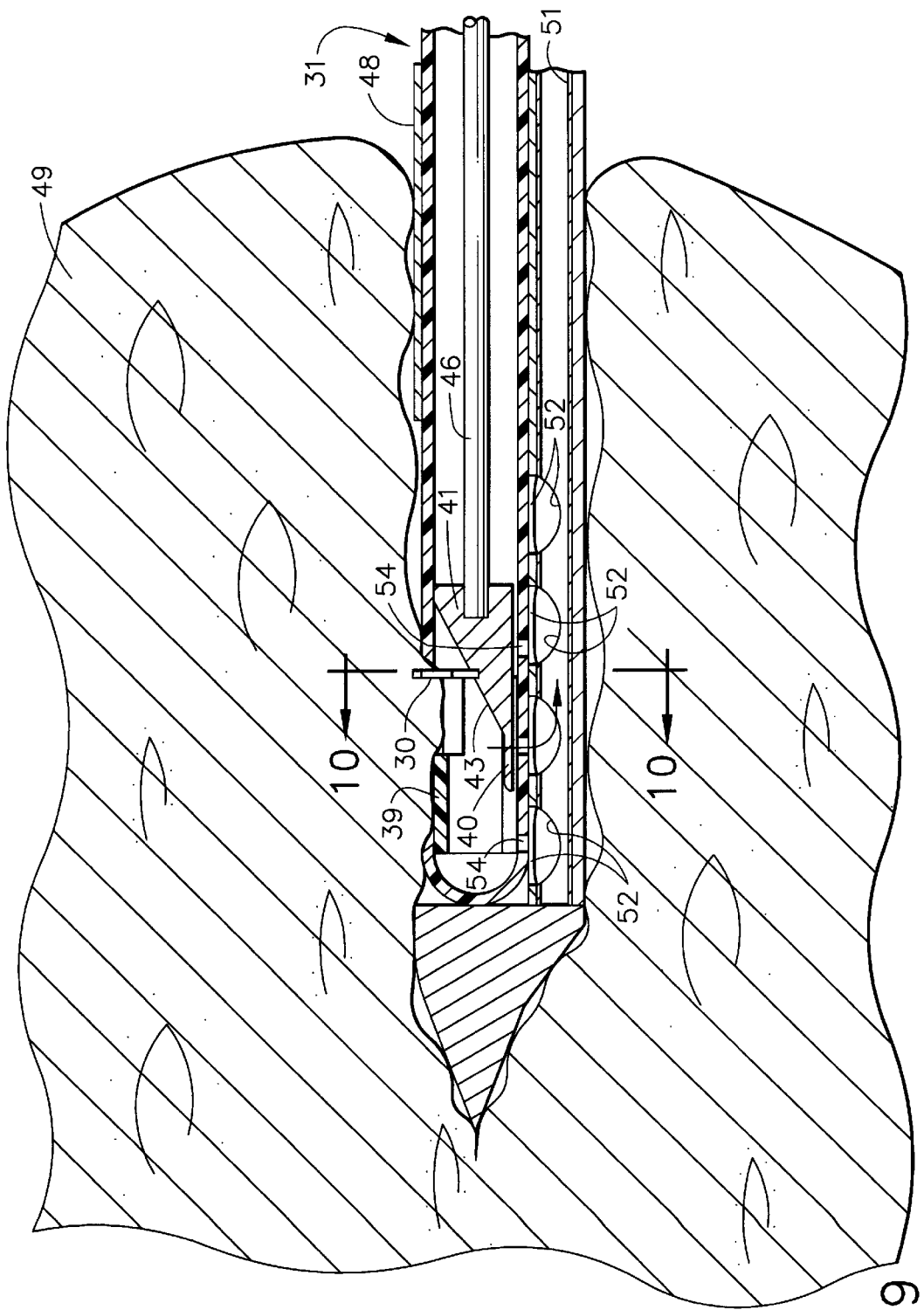
FIG. 9 is a side elevation view in section illustrating the marker being ejected into tissue.

Referring now to FIG. 9, vacuum is applied through the vacuum tube of the biopsy cannula in the direction of the arrow to consequently draw the breast tissue against the marker cannula. Additionally, the push rod 46 is actuated. When the push rod is actuated, it moves longitudinally through the marker cannula in a distal direction. The movement of the push rod in turn moves the ejector shoe 41 in a distal direction. As the ejector shoe moves in a distal direction, the biopsy marker 30 rides on the sloped 43 ramp of the ejector shoe. This in turn causes the biopsy marker to be urged upwardly from within the marker cannula and through the lateral marker window and lateral biopsy window.

Figure 10:
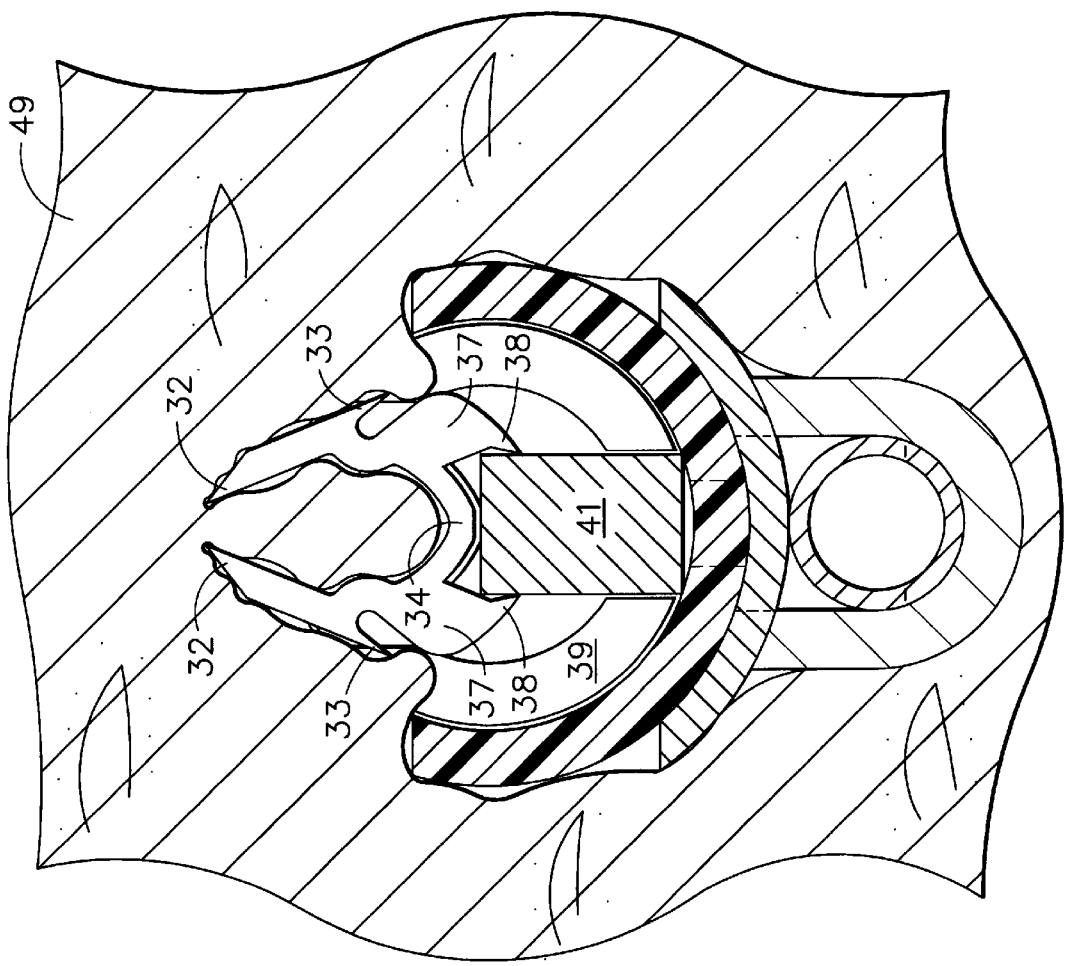
FIG. 10 is a view taken along line 10—10 of FIG. 9 illustrating the closure of the marker as it is ejected into the tissue.
Figure 11:
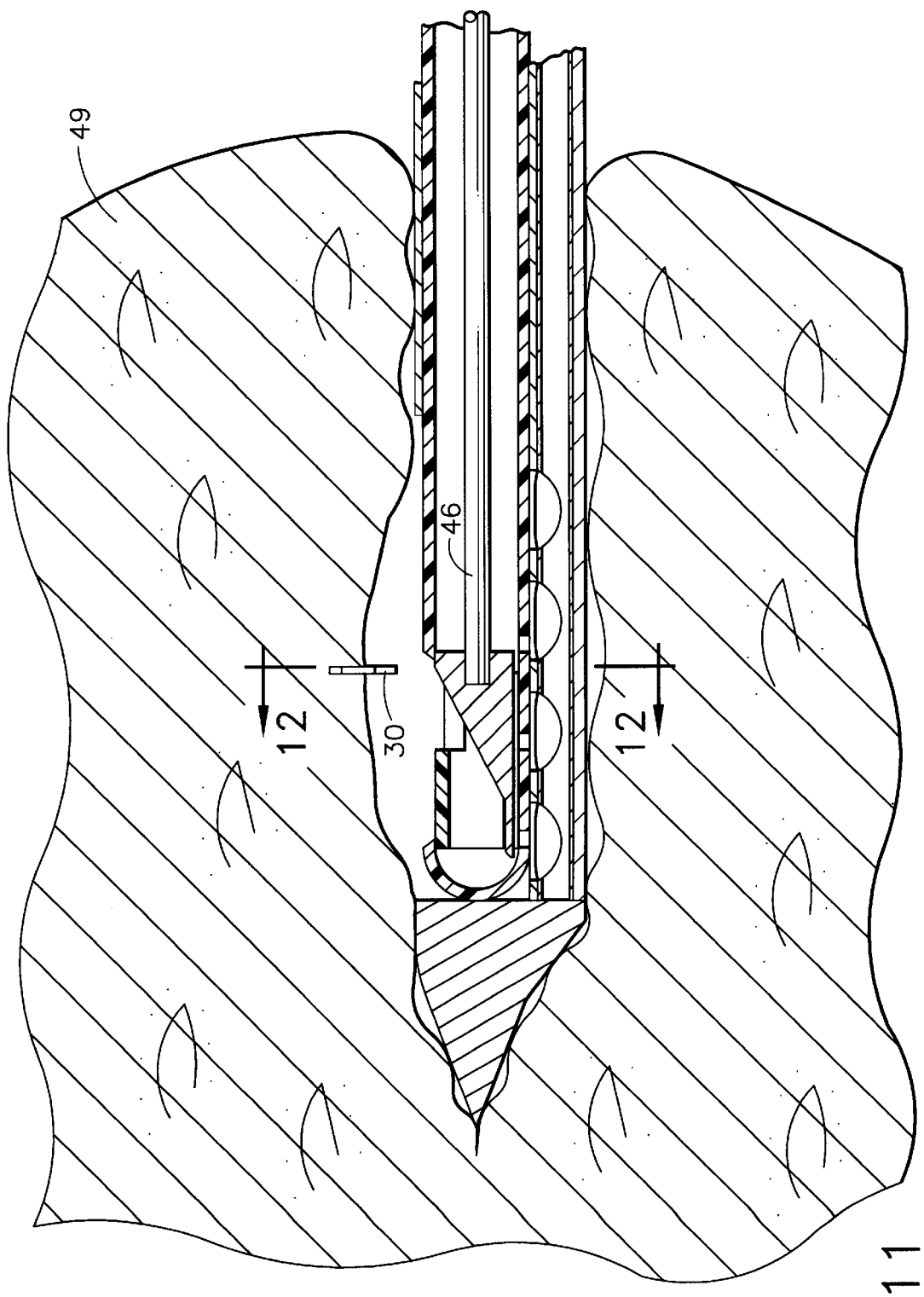
FIG. 11 is another side elevation view in section illustrating the ejection of the marker from the applier.
Figure 12:
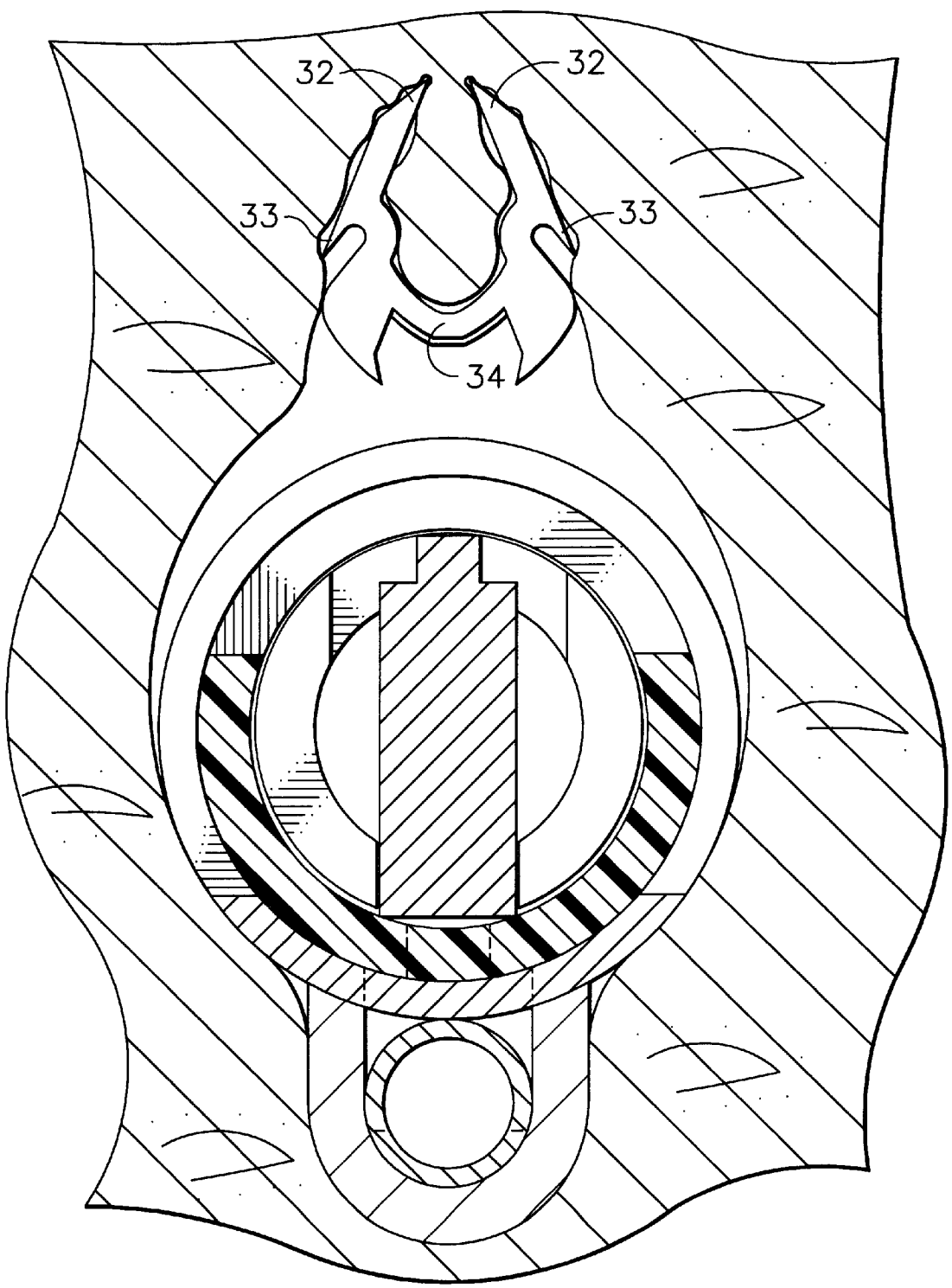
FIG. 12 is a view taken along line 12—12 of FIG. 11 illustrating the implantation of the marker into tissue.
Figure 13:
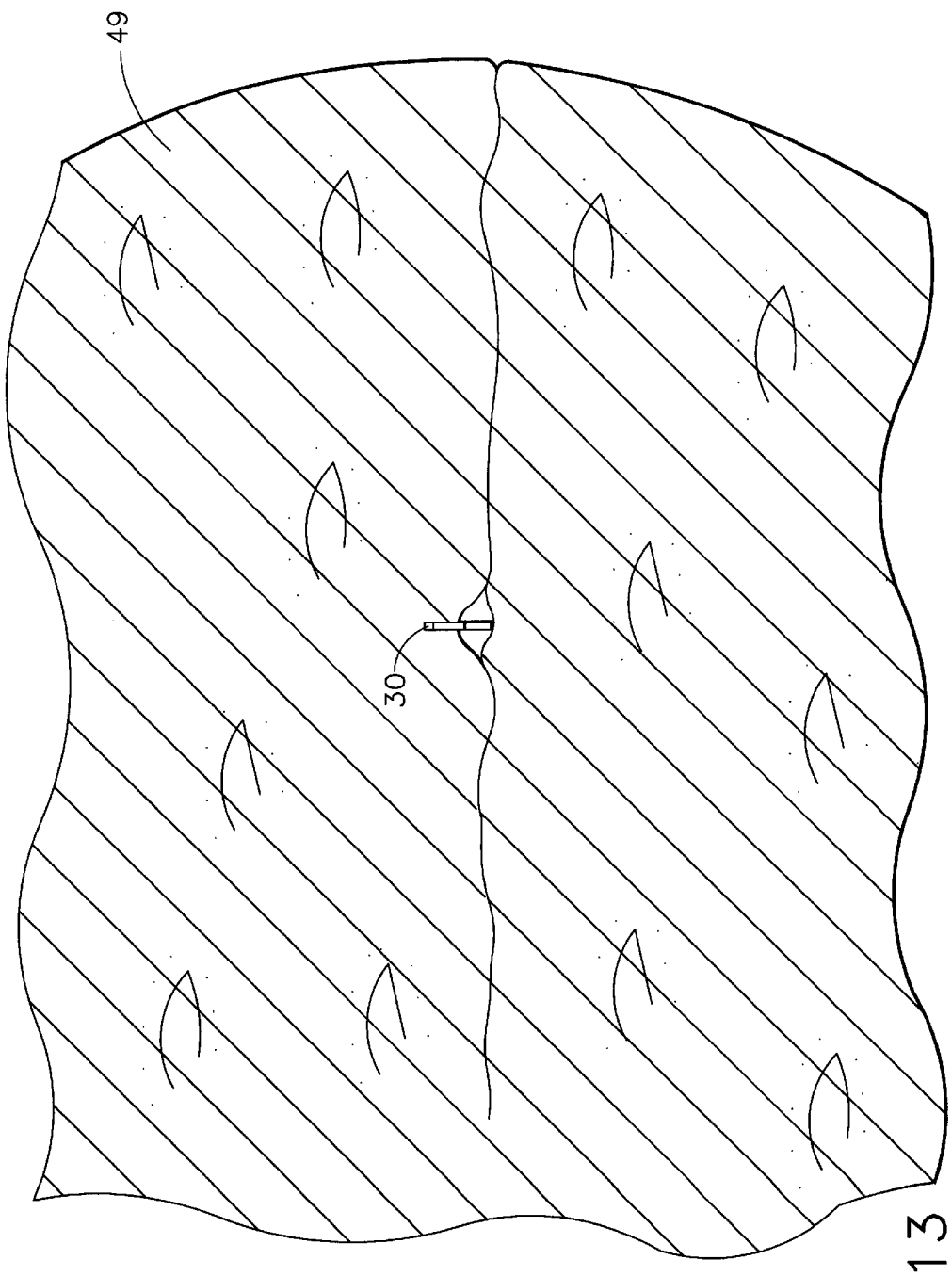
FIG. 13 is a side elevation view of the marker implanted in tissue with the marker applier and biopsy cannula removed.
Figure 14:
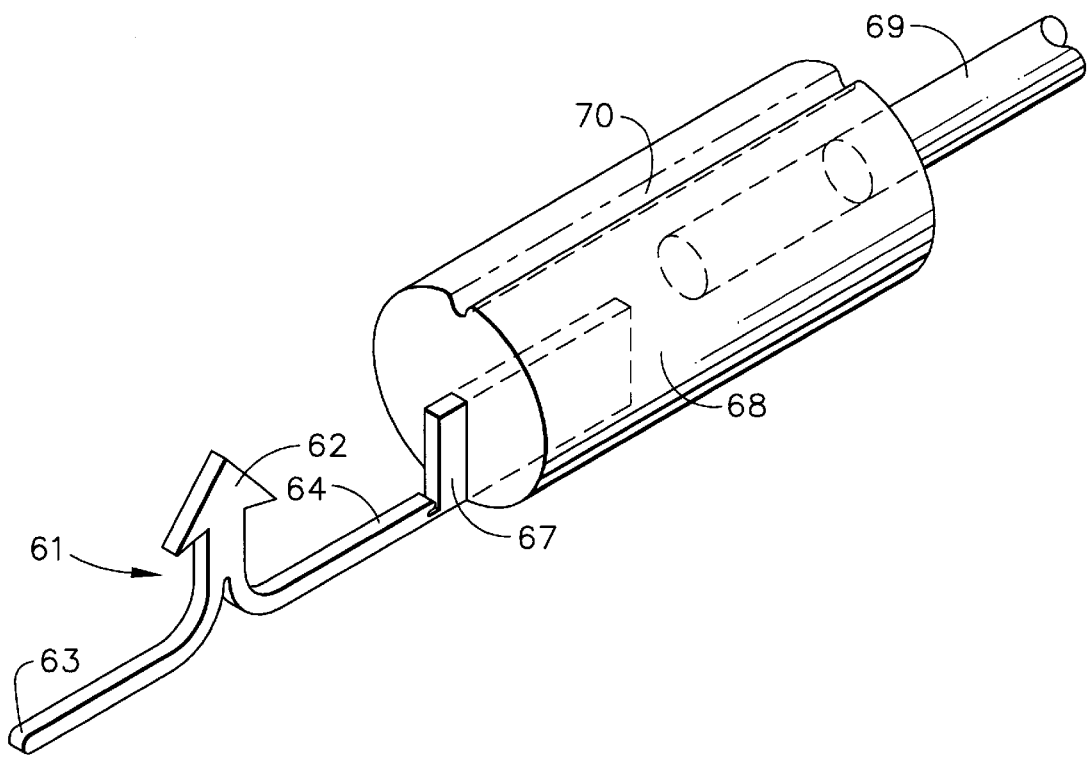
FIG. 14 is an isometric view of an alternate embodiment of a biopsy marker and applier for use with the method of this invention.
Figure 15:
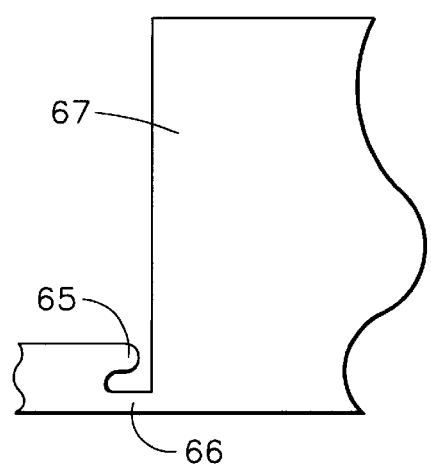
FIG. 15 is a fragmentary and enlarged view of the breakable hinge of the marker of FIG. 14.
Figure 16:
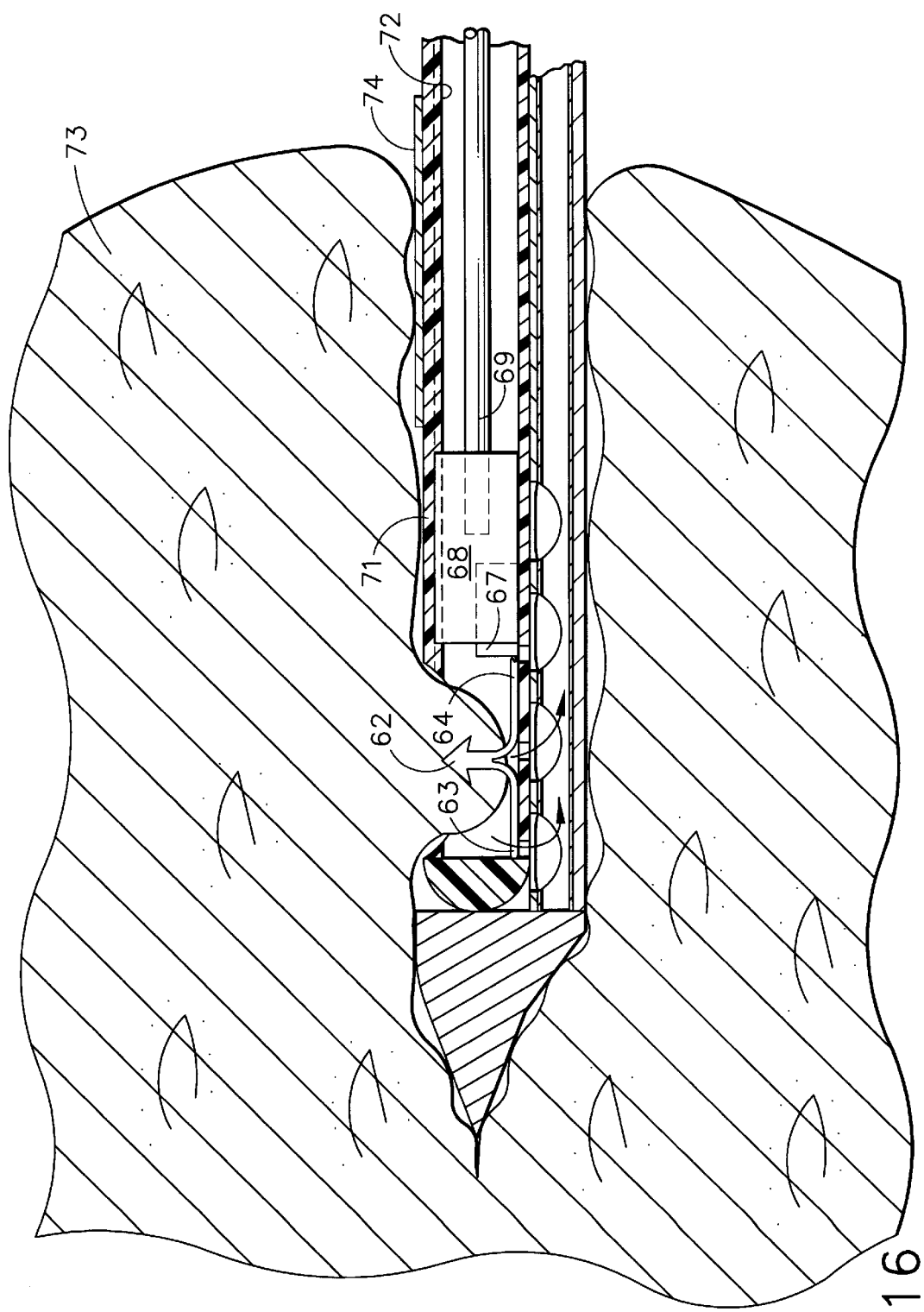
FIG. 16 is a side elevation view in section of the marker applier of FIG. 14 inserted into a biopsy cannula positioned at a breast biopsy site.

Referring to FIG. 10, upon ejection of the biopsy marker from the marker cannula, the reader will observe the conversion of the marker from its original open position to its closed position as the marker is formed by the wedge action of the ejector shoe 41 as the marker is pressed against the marker backstop 39. In looking at FIG. 11, the reader will observe that the biopsy 30 marker has now been implanted in the breast tissue 49. Importantly, the ejection of the biopsy marker was accomplished in a direction substantially perpendicularly to the longitudinal movement of the elongated ejector push rod 46. Also, the reader will observe that once the marker has been implanted, the vacuum which was drawn through the vacuum tube of the biopsy cannula can be stopped. FIG. 12 is another illustration of the fully implanted biopsy marker in the tissue. It is worthy to note how the reverse migration cleats 33 facilitate the prevention of unwanted rearward migration of the implanted marker in the tissue. Finally, in FIG. 13, the marker applier and the biopsy cannula have been removed from the biopsy site after the push rod has been actuated to implant the marker to finish the surgical procedure.

Referring briefly to FIG. 1, the marker applier 31 is illustrated. It features an actuator 55 having an actuator housing 56. A release button 57 and an indicator window 58 are visible on the actuator housing. Upon squeezing the release button, the push rod is actuated for longitudinal movement within the marker applier to eject the biopsy marker from the marker window. Upon ejection, not only will there be audible and tactile feedback confirming the ejection of the marker, but a visual indicator will be readily observable to the user through the indicator window 58. The marker applier also features an orientation hub 59 with a detent 60 to facilitate the proper orientational alignment of the marker window with the lateral biopsy window once the marker applier has been inserted through the biopsy cannula. A more detailed discussion of these particular features of the marker applier can be found in commonly assigned, copending application Ser. No. 09/105,570, filed Jun. 26, 1998, and entitled "Applier For Implantable Surgical Marker".

Another embodiment of a biopsy marker in combination with a marker applier for use with a method of this invention is shown in FIGS. 14–18. The biopsy marker 61 has an upwardly extending piercing element 62 separating a distal leg 63 and a proximal leg 64. The proximal leg has a pivot stop 65 and a breakable hinge 66 connected to a rectangular base 67. The rectangular base is inserted into a cylindrical base 68. The distal end of the ejector push rod 69 is coupled to the cylindrical base. A lateral groove 70 is embedded on the top surface of the cylindrical base. The cylindrical base is received in the marker cannula 71. The cylindrical base can slide longitudinally in the marker cannula in response to the longitudinal movement of the ejector push rod. The marker cannula includes a lateral ridge 72 on its top surface to cooperate with the lateral groove on the top surface of the cylindrical base.

Figure 17:
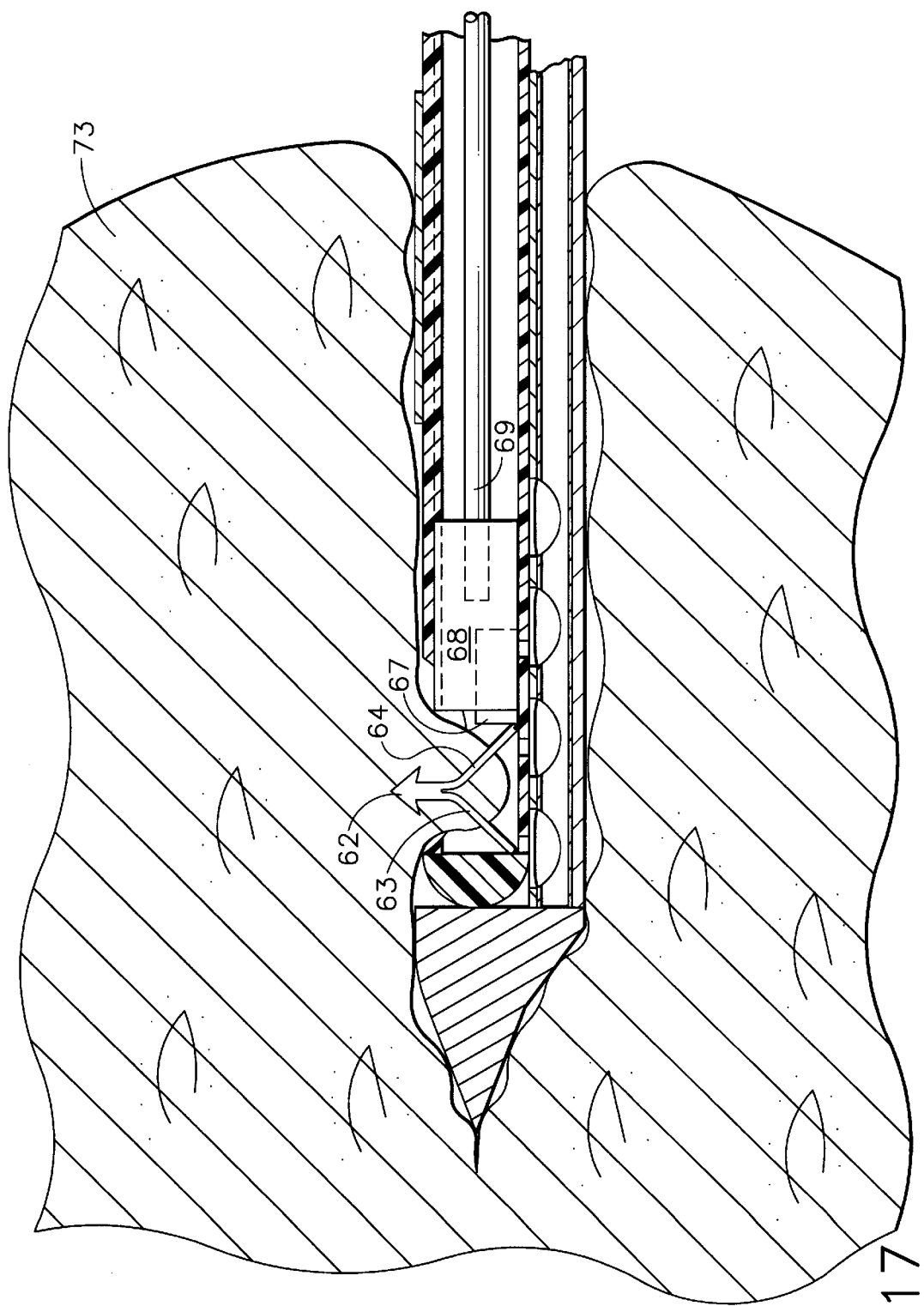
FIG. 17 is a side elevation view in section of the marker of FIG. 14 shown at a mid-ejection position.
Figure 18:
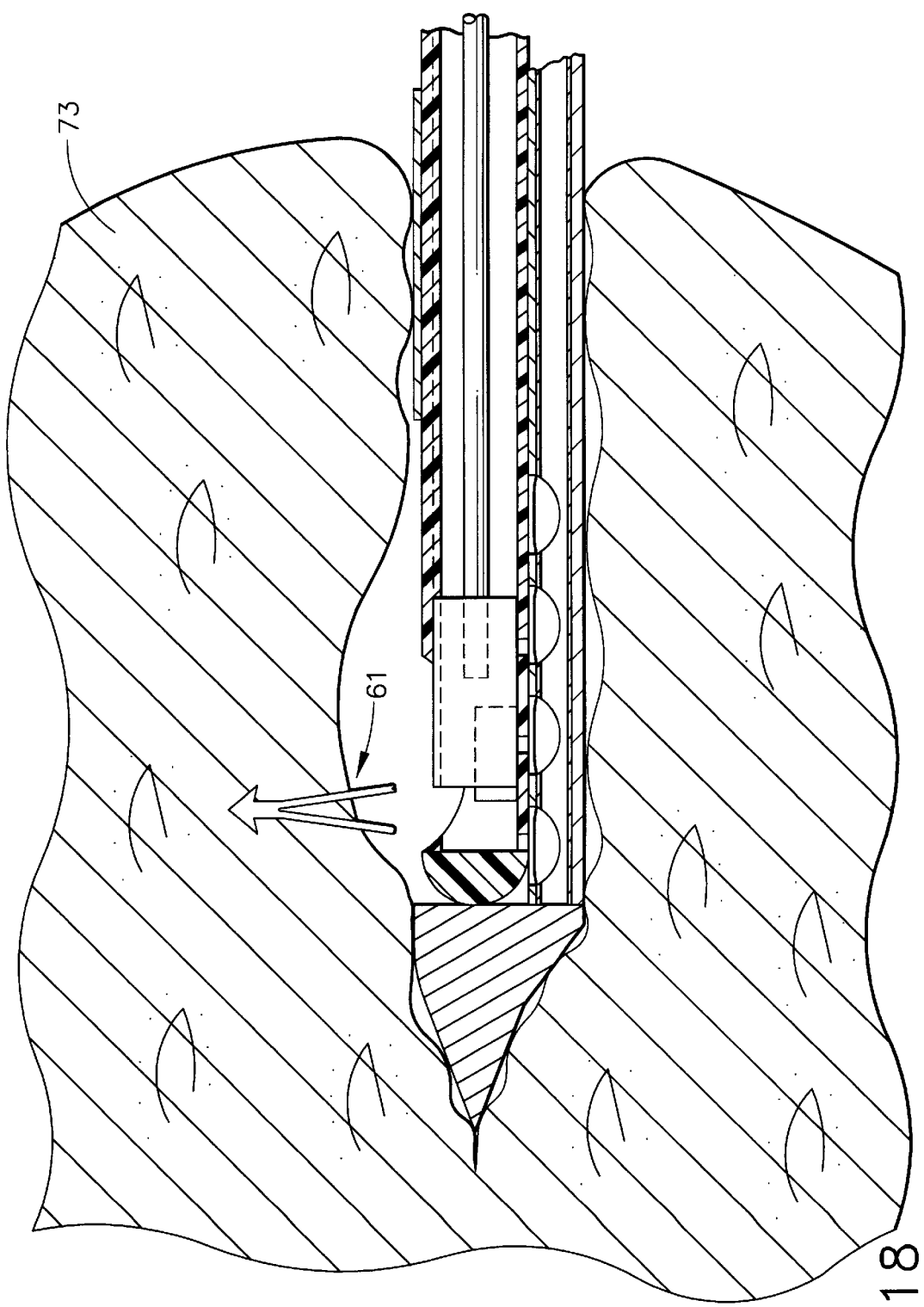
FIG. 18 is a side elevation view in section of the marker of FIG. 17 shown at a post-ejection position.

The piercing element 62 of the biopsy marker 61 and the cylindrical base 68 are initially positioned in the marker cannula so that the piercing element is exposed to the breast tissue 73 through the marker and biopsy windows once vacuum is applied to the vacuum tube of the biopsy cannula 74. As illustrated in FIG. 17, when the ejector push rod 69 is actuated, the cylindrical base 68 correspondingly moves longitudinally in a distal direction, and the distal and proximal legs, 63 and 64, are squeezed together forcing the ejection of the piercing element 62 of the biopsy marker into the breast tissue in a direction substantially perpendicularly to the longitudinal movement of the ejector push rod. Once the biopsy marker has been fully ejected, the breakable hinge of the biopsy marker decouples from the rectangular base 67 embedded in the circular base, and the vacuum can be removed, as depicted in FIG. 18.

Figure 19:
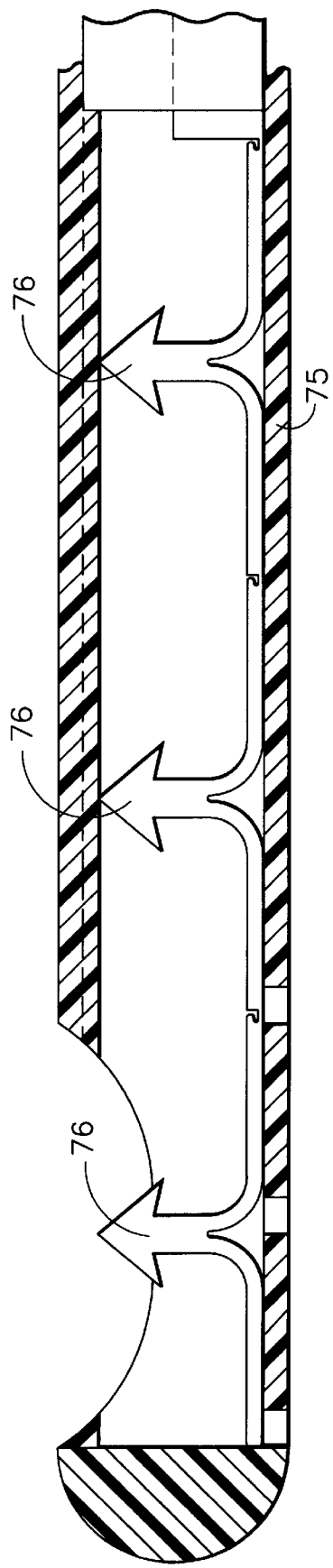
FIG. 19 is a further embodiment of the marker applier of FIG. 14 wherein a plurality of markers is connected in series.
Figure 20:
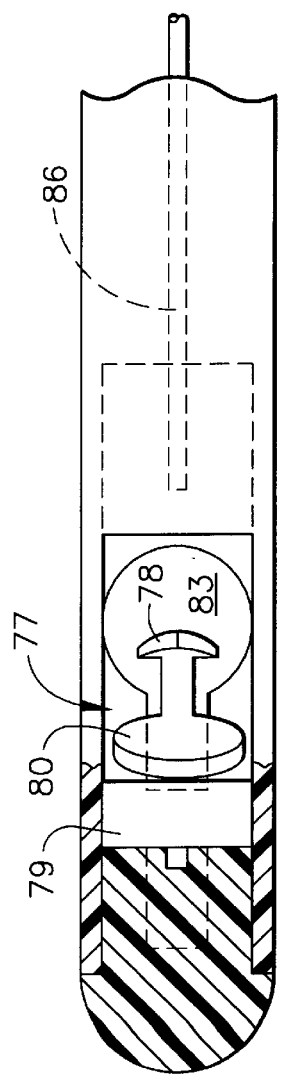
FIG. 20 is a plan view partially cut away of another embodiment of a biopsy marker and applier for use with the method of this invention.
Figure 21:
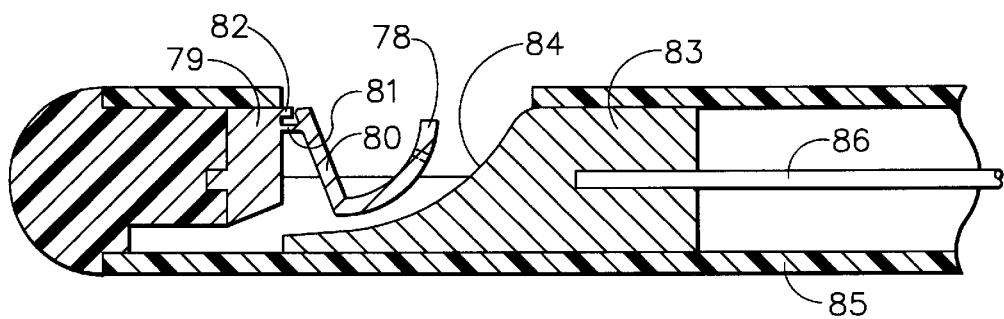
FIG. 21 is a side elevation view in section of the alternate embodiment of the applier of FIG. 20 illustrating the marker in its pre-ejection position.

Referring to FIG. 19, there is illustrated a potentially advantageous modification of the marker and marker applier combination shown in FIGS. 14–18. Specifically, the reader will note that the marker cannula 75 can receive a plurality of biopsy markers 76, and the ejector push rod can be cooperable with these biopsy markers to eject each of the biopsy markers individually in series.

Figure 22:
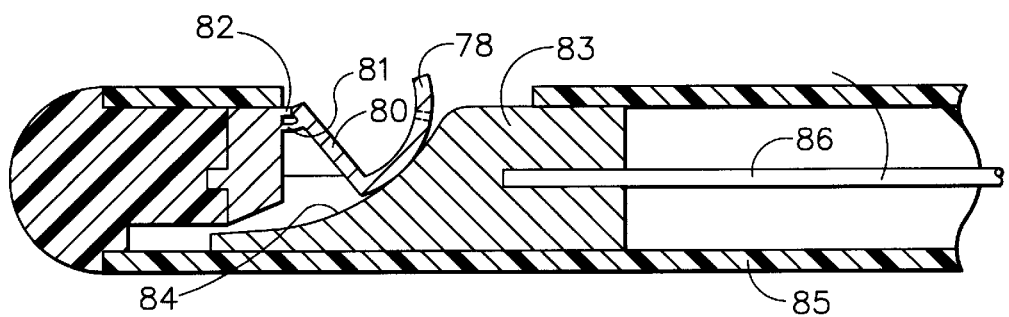
FIG. 22 is a side elevation view in section of the applier of FIG. 21 illustrating the marker at a mid-ejection position.
Figure 23:
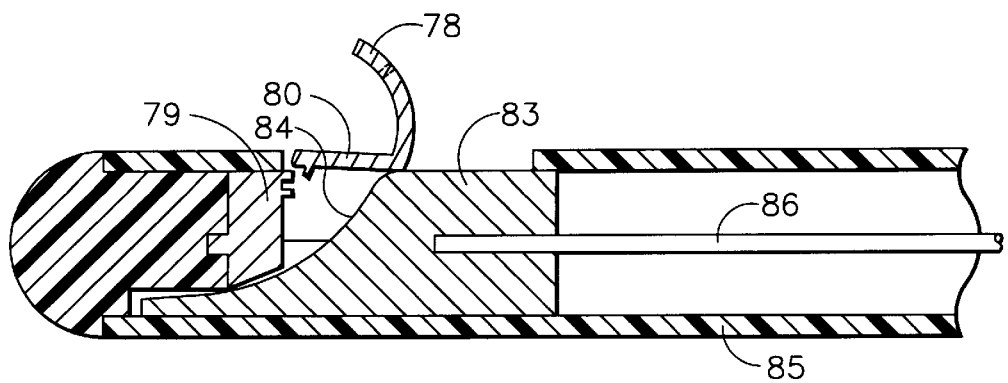
FIG. 23 is a side elevation view in section of the applier of FIG. 24 illustrating the marker in the post-ejection position.

In another embodiment depicted in FIGS. 20–23, the biopsy marker 77 has a penetrating portion 78 and a base 79. Interposed between the penetrating portion and the base is a circular tab portion 80 and a breakable hinge 81 coupling the circular tab portion to the base. The base also includes a hinge stop 82. An ejection shoe 83 with a downwardly sloping ejection ramp 84 is positioned in the marker cannula 85 at the lateral marker window. The ejection shoe is coupled to the distal end of the ejector push rod 86. Upon actuation of the ejector push rod 86, the downwardly sloping ejection ramp comes into contact with the arcuate stem of the penetrating portion 78 of the biopsy marker upon distal movement of the ejection shoe. This movement creates a torque at the hinge 81 and the penetration portion moves upwardly through the marker and biopsy windows in a direction substantially perpendicularly to the longitudinal movement of the ejector push rod. As depicted in FIG. 22, as the penetrating portion of the biopsy marker moves upwardly in response to its sliding movement on the downwardly sloping ramp of the ejection shoe, the circular tab portion of the marker comes into contact with the hinge stop. Upon completing its upward movement, the breakable hinge of the biopsy marker snaps off from its base, and the biopsy marker has now been fully ejected from the marker and biopsy windows.

Figure 24:
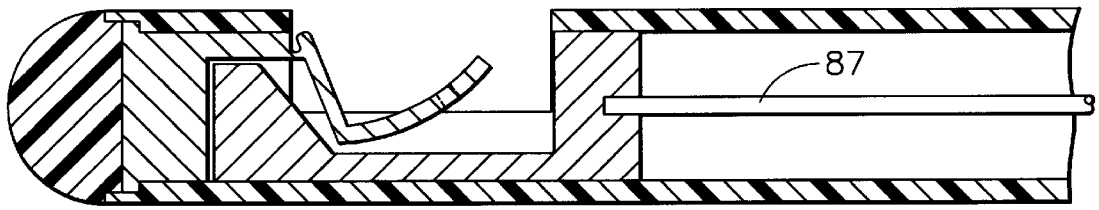
FIG. 24 is a side elevation view in section of another alternate embodiment of a marker and applier for use with the method of this invention.
Figure 25:
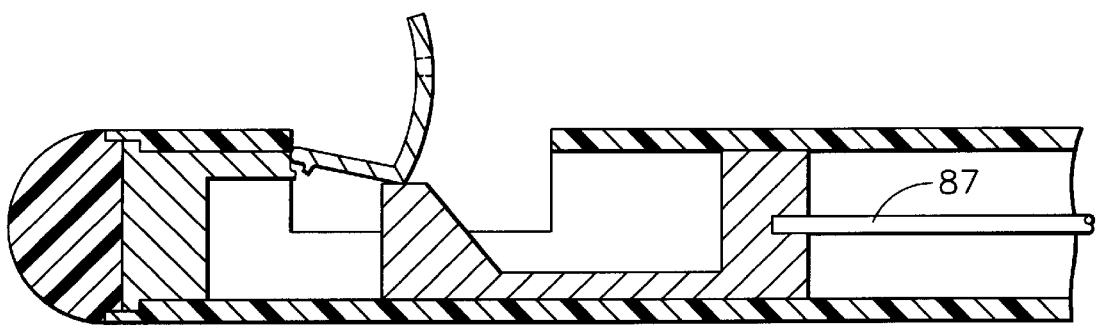
FIG. 25 is side elevation view in section of the applier of FIG. 24 illustrating the marker in the ejected position.

In yet another embodiment of the marker in combination with the marker applier, a variation of the embodiment depicted in FIGS. 20–23 is depicted in FIGS. 24 and 25. In this particular embodiment, the reader will observe that the ejector rod 87 works as a pull rod. Consequently, upon actuation of the pull rod, the rod moves longitudinally in a proximal direction to eject the biopsy marker from the marker and biopsy windows.

Although this invention has been described in connection with its most preferred embodiments, these embodiments are exemplary only and are not intended to limit the scope or spirit of the claimed invention. Numerous additional embodiments will become readily apparent to those skilled in this art. The scope of the invention is defined solely by the claims which appear below.

What is claimed is:

1. A method for implanting a biopsy marker at a surgical site within bodily tissue, said method comprising:

a) providing a marker applier having:

i) a marker cannula for receiving said biopsy marker in said marker cannula, said marker cannula having a lateral marker window at a distal end of said marker cannula, and said biopsy marker is positioned at said lateral marker window for ejection out of said lateral marker window; and ii) an elongated ejector rod moveable longitudinally in said marker cannula, said ejector rod cooperable with said biopsy marker for ejecting said biopsy marker out of said lateral marker window in a direction substantially perpendicular to said elongated ejector rod upon a lateral movement of said ejector rod;

b) inserting said marker applier into a biopsy cannula positioned at the biopsy site, said biopsy cannula having a vacuum tube port and a lateral biopsy window at a distal end of said biopsy cannula, wherein said marker cannula of said marker applier has a cannula port in communication with said vacuum tube port;

c) orienting said lateral marker window of said marker cannula of said marker applier into alignment with said lateral biopsy window of said biopsy cannula;

d) pulling vacuum through said vacuum tube port so as to draw the bodily tissue at the biopsy site adjacent to said lateral biopsy window of said biopsy cannula; and e) actuating said elongated ejector rod of said marker applier for longitudinal movement of said ejector rod in said marker cannula so as to eject said biopsy marker in a direction substantially perpendicular to said elongated ejector rod:

i) from said marker cannula, ii) through said lateral marker window and said lateral biopsy window; and iii) into the bodily tissue at the biopsy site.

2. The method of claim 1 further comprising the step of removing said marker applier from the biopsy site after the step of actuating said ejector rod.

3. The method of claim 1 wherein the bodily tissue is the breast, and the biopsy site is a site of a breast biopsy.

4. The method of claim 1 wherein said ejector rod is a push rod, and when said push rod is actuated, said push rod is moved distally in said marker cannula to eject said biopsy marker.

5. The method of claim 1 wherein said ejector rod is a pull rod, and when said pull rod is actuated, said pull rod is moved proximally in said marker cannula to eject said biopsy marker.

6. The method of claim 1 wherein said marker cannula receives a plurality of biopsy markers, and said ejector rod is cooperable with said biopsy markers to eject each of said biopsy markers individually in series.

* * * * *